United States Patent [19]

Bauman

[11] Patent Number: 4,652,520
[45] Date of Patent: Mar. 24, 1987

[54] COMPARATIVE ASSAY METHOD AND DEVICE

[75] Inventor: David S. Bauman, Norman, Okla.
[73] Assignee: Immuno-Mycologics, Inc., Norman, Okla.
[21] Appl. No.: 631,488
[22] Filed: Jul. 16, 1984
[51] Int. Cl.⁴ ............................................. G01N 33/58
[52] U.S. Cl. ...................................... 435/34; 435/291;
435/808; 422/57; 422/81; 436/527; 436/805
[58] Field of Search .................... 435/291, 808, 34, 29;
422/57, 83, 88, 91, 69, 81; 424/2; 436/527, 805, 807, 808

[56] References Cited

U.S. PATENT DOCUMENTS

| | | | |
|---|---|---|---|
| 3,838,011 | 9/1974 | Hagen | 422/81 X |
| 3,973,911 | 8/1976 | Swolinski | 422/91 |
| 4,425,438 | 1/1984 | Bauman | 436/527 |

*Primary Examiner*—Alan Cohan
*Attorney, Agent, or Firm*—Laney, Dougherty, Hessin & Beavers

[57] ABSTRACT

A method and device for performing comparative assay of binding and bindable substances such as antibodies and antigens. The device includes a circulation conduit for continuously conveying a carrier fluid between a support zone therein and a detection zone therein. A competitive binding substance is fixed in the support zone and is capable of competitively binding a test substance and an analytical detection substance such that changes in concentration of the test substance in the carrier fluid responsively cause changes of concentration of analytical detection substance in the carrier fluid. Each of the analytical detection substance (antigen-fluorochrome, for example) and the test substance (antigen, for example) are bound to the binding substance (monoclonal antibody, for example) in proportion to the concentration of the test substance in the carrier fluid. A detection means is provided for detecting changes in the concentration of the analytical detection substance as the carrier fluid is conveyed through the detection zone. Preferably, the detection means comprises a fluorescent detector detecting fluorescent activity produced by the fluorochrome detection substance. The fluorescent detector includes a comparator which compares the degree of fluorescent activity in a lo-flow tube compared to a hi-flow tube. Changes in concentration of the test substance produce a variation in the fluorescent activity in the hi-flow tube compared to the lo-flow tube. The method includes introducing a test substance into the carrier fluid of a device of the type described above. A comparative assay is performed by detecting changes in the concentration of the analytical detection substance produced by the introduction of the test substance.

16 Claims, 1 Drawing Figure

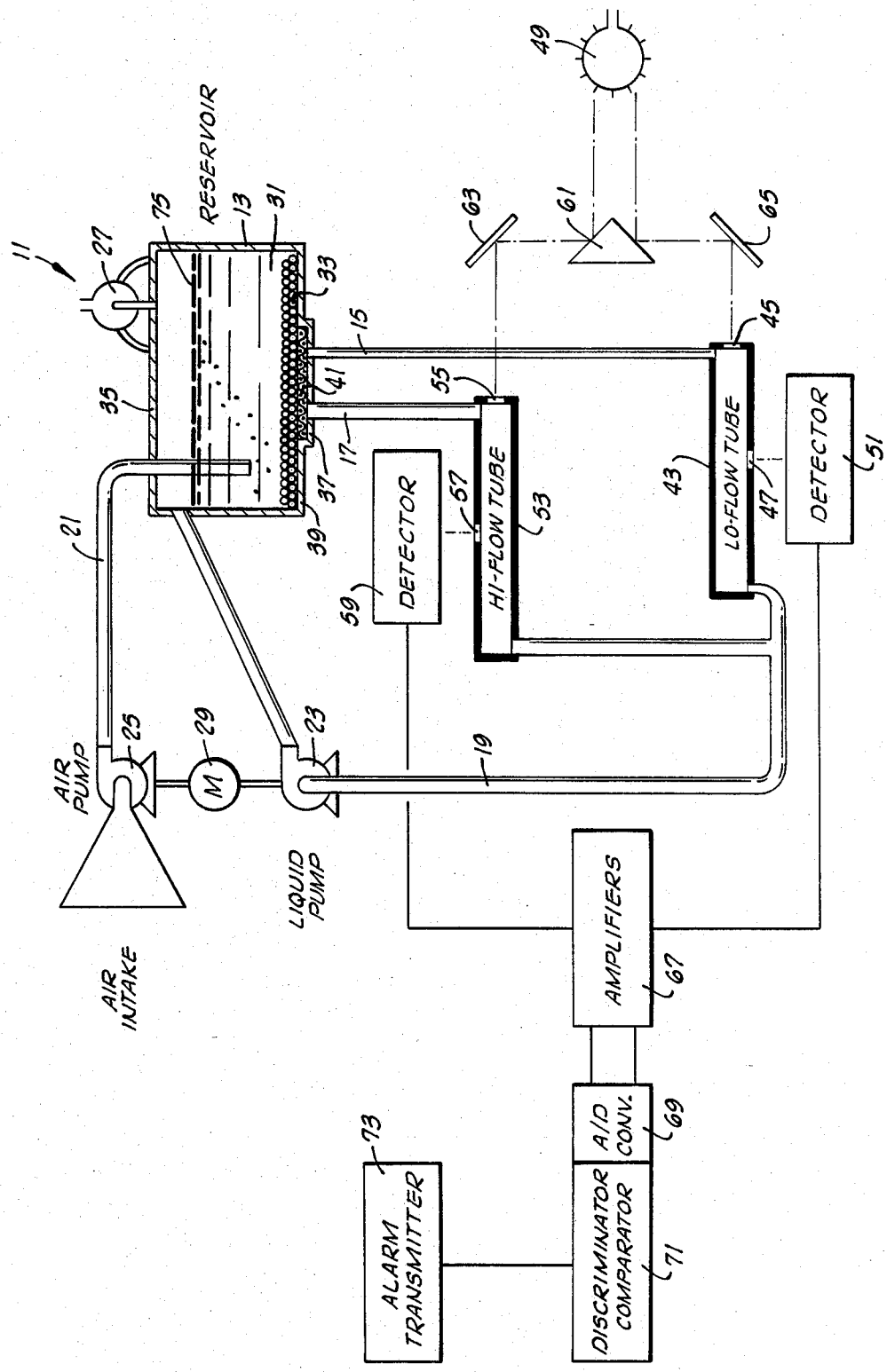

COMPARATIVE ASSAY METHOD AND DEVICE

BACKGROUND OF THE INVENTION

1. Field of the Invention

This invention relates in general to devices and methods for determination of substances and, more particularly, to methods and devices for assays of binding or bindable substances. Still further, this invention relates to a comparative method and device for a comparative assay of such binding or bindable substances.

2. Description of the Prior Art

In the past, many tests have been provided for determination of binding and bindable substances of various types. Examples of such binding and bindable substances and the substances bound thereto or thereby are antibody-antigens and other binding proteins-protein bindable substances.

An example of a particular type of assay device and method used in the past is described in U.S. Pat. No. 3,654,090 to Schuurs et al. This patent describes a test for determination of either an antigen or an antibody. In one example of the U.S. Pat. No. 3,654,090, a quantity of antigen is attached to an enzyme and a quantity of antibody is insolublized by attachment to insoluble carrier. The enzyme-label antigen and the insolublized antibody are mixed with an unlabelled antigen (the assay substance). By controlling the amount of insolublized antibody and enzyme-labelled antigen, some or all of the enzyme-labelled antigen is not attached to antibody when unlabelled antigen is present. Some or none of the enzyme-labelled antigen is attached. After mixing, the insoluble material is separated from the soluble material which includes any unattached enzyme-labelled antigen. Centrifuging or washing the insoluble material achieves this separation. An enzyme-reactive agent is then added to either the insoluble or soluble portions to assay the enzyme activity. In this manner, the presence of unlabelled antigen (the assay substance) is determined.

Other patents showing similar processes for the determination of binding or bindable substances are shown in U.S. Pat. Nos. 3,791,932 to Schuurs et al; 3,839,153 to Schuurs et al; 3,850,752 to Schuurs et al and 4,016,043 to Schuurs et al. Each of these patents show one component labelled with an enzyme and another made insoluble. As described in U.S. Pat. No. 3,966,897 to Wren et al, the same types of competitive and non-competitive bio-assay processes have been performed by radioactive labelling as opposed to enzyme labelling. Further, as opposed to either radioactive labelling or enzyme labelling, indicator dyes, fluorimetry, spectrofluorotometry or refractomotry can be utilized to measure the assay.

A quantitative assay method and device are described in U.S. Pat. No. 4,425,438 issued Jan. 10, 1984, and assigned to the assignee of the present invention. The quantitative assay device described therein includes a funnel having retained therein glass beads with a competitive binding substance such as a monoclonal antibody affixed thereto. An analytical reagent, such as an enzyme-tagged antigen specific to the monoclonal antibody, is passed over the glass beads such that the reagent is attached and held by the antibodies. Then, if a fluid containing a test substance which competitively binds to the antibodies is passed over the beads, some of the analytical reagent is displaced. The amount of displaced analytical reagent is proportional to the amount of test substance. The amount of analytical reagent is then quantitatively assayed by means of a linear zone of analytic reagent binder. The length of zone colored by an enzyme active coloring agent indicates the quantity of test substance which has been passed over the glass beads in the funnel.

While the above devices have been useful for quantitative and qualitative assays, they are not useful for a comparative assay. Thus, they cannot be utilized to continuously monitor or determine the presence or absence of binding or bindable substances in media such as air or water. Also, the above devices and methods are not satisfactory for completely automated operation. Thus, a technician must operate the equipment and perform the methods for each assay.

SUMMARY OF THE INVENTION

It is accordingly an object of the present invention to provide an improved comparative assay method and device.

It is also an object of the present invention to provide an improved assay method and device for continuously monitoring and detecting the presence or absence of a test substance.

Still another object of the present invention is to provide an assay method and device which do not require human participation in order to indicate the presence or absence of a test substance.

In accordance with the objects, the present invention provides a device for assaying a test substance for comprising a circulation conduit for conveying a carrier fluid between a support zone and a detection zone located therein. A circulation means circulates the carrier fluid between the support zone and the detection zone. A competitive binding substance is fixed in the support zone and is capable of competitively binding a test substance and an analytical detection substance such that changes in concentration of test substance in the carrier fluid responsively cause changes of concentration of the analytical detection substance in the carrier fluid since each of the analytical detection substance and the test substance are bound to the binding substance in proportion to the concentration of the test substance in the carrier fluid. A detection means is provided for detecting changes in concentation of the analytical detection substance in the carrier fluid as the carrier fluid is conveyed through the detection zone. An introduction means is provided for introducing the test substance into the carrier fluid.

Preferably, the carrier fluid comprises a buffered liquid and the circulation means comprises a liquid pump for continuously circulating the liquid in the circulation conduit. The introduction means preferably comprises an air conduit extending into the circulation conduit and an air pump for moving air through the air conduit into the carrier fluid and the circulation conduit. By these means, airborne antigens, for example, are introduced to the circulating carrier liquid in the device and become dissolved therein. If the airborne antigen is a test substance which competitively binds with the analytical detection substance on the competitive binding substance, some of the analytical detection substance will be displaced changing the concentration of the analytical detection substance in the carrier fluid. This changed concentration fluid is then conveyed to the detection means which detects the change in concentration which also indicates that a test substance, such as an antigen, has been introduced to the device.

Since the fluid can continuously or at least automatically operate, and the detection is of changes in concentration as opposed to a qualitative detection, the device can automatically operate for assaying without the presence of a technician.

The analytical detection substance preferably comprises a fluorochrome coupled to a competitive binding agent and the detection means comprises a fluorescence detector. Further, the detection zone of the circulation conduit preferably comprises a low flow fluorescence tube allowing only a relatively low flow rate of carrier fluid therethrough and a high flow fluorescence tube allowing a relatively high flow rate of carrier fluid therethrough. A low flow fluorescence detector detects the degree of fluorescence activity in the low flow fluorescence tube and a high flow fluorescence detector detects the degree of fluorescence activity in the high flow fluorescence tube. The comparator means then compares the fluorescence activity detected by the low flow fluorescence detector and the fluorescence activity detected by the high flow fluorescence detector so as to indicate a changing concentration of fluorochrome in the carrier fluid caused by the introduction of a test substance into the carrier fluid by means of the introduction means. The comparator can then be connected to an alarm for signalling when changes in concentration of the analytical detection substance in the carrier fluid occur. Such an alarm would, for example, alert persons to the presence of airborne poisons or diseases.

The method of the present invention comprises conducting an assay on a test substance by means of circulating a carrier fluid between a support zone and a detection zone. In the support zone, a competitive binding substance is fixed which competitively binds an analytical detection substance and a test substance such that changes in concentration of the test substance in the carrier fluid responsively cause changes in concentration of the analytical detection substance in the carrier fluid. In the detection zone changes in concentration of the analytical detection substance can be detected. The method includes introducing a test substance into the carrier fluid and detecting changes in concentration of the analytical detection substance in the carrier fluid as the carrier fluid is circulated through the detection zone. As can be seen, the method of the present invention can be accomplished by introducing a test substance into the device of the present invention.

For a further understanding of the invention and further objects, features and advantages thereof, reference may now be had to the following description taken in conjunction with the accompanying drawing.

BRIEF DESCRIPTION OF THE DRAWINGS

The FIGURE illustrates a schematic view of the assay device of the present invention.

DESCRIPTION OF PREFERRED EMBODIMENTS

In order to perform the comparative assay for a test substance, the present invention utilizes a competitive binding substance and an analytical detection substance. Each of these substances are chosen for each other and the test substance. Furthermore, each must have certain properties in order for the comparative assay and the assay device to function.

The competitive binding substance must be capable of competitively binding a test substance and the analytical detection substance such that changes in concentration of the test substance in a carrier fluid passing over the competitive binding substance cause changes of concentration of the analytical detection substance in the carrier fluid due to competitive binding. In other words, since each of the analytical detection substance and the test substance are bound by the competitive binding substance and compete for binding, if not all of the test substance and the analytical detection substance can be bound then a proportional amount of each is bound. By changing the concentration of the test substance in the carrier fluid this proportion is changed so that the concentration of analytical detection substance in the test fluid changes as well.

The competitive binding substance must also be capable of being fixed in a support zone so that fluid can be passed over, through and contacted with the competitive binding substance.

The test substance and the analytical detection substance must be capable of competing for binding by the competitive binding substance as described above. Further, the analytical detection substance must have the capability of being selectively being detected. Further, it must be capable of being detected in a manner so that the concentration changes as opposed to merely presence or absence may be detected.

There are a wide variety of substances which meet the requirements described above. There are also a wide variety of well-known processes for producing these substances.

Substances which meet the requirements for a test substance include antigens, antibodies and various other organic substances. Since the most important requirement of the test substance is that the test substance be capable of being competitively bound by a competitive binding substance, those skilled in the art will recognize that a binding substance for competitively binding most substances can be prepared.

A wide variety of competitive binding substances having the properties described above, are possible. Of course, the competitive binding substance will depend upon the test substance which must be bound by the competitive binding substance. Thus, competitive binding substances for antigens or organic molecule assays would include antibodies and lectins specific for the molecule to be assayed. For example, antibodies against specific microbial antigens, proteins, hormones, polysacrides, antibodies, toxins, etc. could be used for the competitive binding substance. Also, lectins with specific binding activity for sugars, enzyme cofactors, polysacrides, etc. could be used. Competitive binding substances for antibody assays could include antigens or antiorganic compounds for which the antibody is specific. For example, microbial antigen, protein, hormones, polysacrides, antibiotic, toxin, etc. having specific binding activity with the antibody to be assayed could be used.

While it is possible that analytical detection substances may exist without preparation, a simple way of preparing an analytical detection substance specific for a test substance is to utilize the test substance coupled to a detectable group or molecule. For example, if the test substance is an antigen, the antigen could be coupled to a detectable group such as a fluorochrome. Other detectable groups include colored dye, enzymes, radioisotopes and others. Particular enzymes include horseradish peroxidaze, alkaline phosphate, belactosidaze and others. Examples of colored dyes are amedo black and eosen. Radioisotopes include carbon 14 and iodine 125.

For the purpose of the present invention a preferred detectable group comprises fluorescent compounds. This is because the present invention is especially adapted for remote or automatic use and requires comparative as opposed to qualitative detection. Fluorescent compounds or fluorochromes include fluorescein isothiocyanate, dansyl, and others.

Methods for coupling fluorochromes to various chemical agents or test substances are well known to those in the art and depend upon the particular chemical agent or test substance chosen. A representative method of such coupling comprises connecting the test substance or agent with a spacer group such as 1, 3-diaminopropane with cross-linking inhibited by a large excess of diaminopropane. The spacer group is then coupled with the fluorochrome. The choice of coupling chemicals depends upon the particular reactive groups available on the particular agent or test substance.

An example coupling to fluorescein isothiocyanate could occur in 0.1 molar, pH 9 bicarbonate buffer followed by removal of unbound fluoroscein by chromotography through Sephadex G-25. Preparation of antigens or antibodies for coupling to spacer groups are well-known. For example, antigens can be prepared from culture cells by disrupting the cells by freeze/thaw, removal of nuceleae and ribisomes by differential centrifugation, solubilizing with SDS, followed by dialysis.

Other methods of attaching detectable groups of various types to antigens or antibodies are described in U.S. Pat. No. 4,425,438 issued on Jan. 10, 1984, and assigned to the assignee of the present invention. The disclosure of the U.S. Pat. No. 4,425,438 is hereby incorporated herein for a better understanding of the invention and methods of achieving the invention.

A preferred competitive binding substance comprises monoclonal antibodies. Monoclonal antibodies are preferred since they can be specific for a single antigen eliminating the possibility of false readings when antigens other than the test substance are introduced to the method or device of the present invention.

Methods of preparing desired monoclonal antibodies specific to various antigens are well-known. Also, methods of coupling such monoclonal antibodies to soluble supports are well-known. For example, methods of coupling monoclonal antibodies to insoluble supports are shown in U.S. Pat. No. 4,425,438 issued Jan. 10, 1984, and assigned to the assignee of the present invention.

Referring now to the FIGURE a device in accordance with the present invention is shown generally at 11. The device 11 includes a reservoir 13, a low flow conduit 15, a high flow conduit 17, a return conduit 19 and an air intake conduit 21. A liquid pump 23 moves liquid from the reservoir 13 in parallel through the low and high flow conduits 15 and 17 and then returns the liquid to the reservoir 13. An air pump 25 draws air from the environment and moves it through air intake conduit 21 into reservoir 13. The air exits the reservoir 13 through a vent/trap 27. The vent/trap prevents liquid from splashing out of the reservoir while allowing air to exit the reservoir. A motor 29 drives both the air pump 25 and the liquid pump 23.

The reservoir 13 functions as the container for the major portion of the liquid 31 circulated in the device 11. It also serves as the retainer and support for glass beads 33 on which the competitive binding substance is fixed. Still further, it receives the air intake conduit 21 in such a manner that the air is bubbled through the liquid 31 and the reservoir 13. The vent/trap 27 is connected to the top 35 of the reservoir 13. High and low flow conduits 15 and 17 are connected to a recessed portion 37 in the bottom 39 of reservoir 13 so as to receive liquid exiting the reservoir 13. A screen or filter 41 in the recessed portion 37 prevents the glass beads from entering the high and low flow tubes 15 and 17.

A portion of the low flow conduit 15 forms a lo-flow tube 43. The interior of the lo-flow tube 43 is mirrored except for windows 45 and 47 so that the tube can more effectively function as a fluorescent tube. Light from a light source 49 can enter the lo-flow tube 43 through window 45 and light from the interior of the tube 43 can exit the tube through window 47. The window 47 includes a filter which blocks excitation wavelength light from the source 49 while allowing passage of fluorescent wavelength light. A detector 51 is provided adjacent to window 47 for producing a signal proportional to the fluorescent activity received through window 47.

A portion of the high flow conduit 17 forms a hi-flow tube 53. The hi-flow tube 53, like the lo-flow tube 43 is silvered on its interior and has windows 55 and 57 for the entrance and exit of light producing and produced from fluorescent activity. A detector 59 is disposed adjacent window 57 to receive fluorescent activity light from hi-flow tube 53 and produce a signal proportional to the fluorescent activity.

In order to be able to properly compare the fluorescent activity in the hi-flow tube 53 to the fluorescent activity in the lo-flow tube 43 a splitter prism 61 and mirrors 63 and 65 convey the light from source 49 through both the windows 45 and 55. It can thus be assured that variations in the light source do not produce differences in the fluorescent activity in the lo-flow tube 43 versus the hi-flow tube 53.

As described above, the detectors 51 and 59 produce signals, preferably electrical signals proportional to the amount of fluorescent activity occuring in the lo-flow tube 47 and the hi-flow tube 53, respectively. These signals are conveyed to an amplifier 67 where they are separately amplified and then conveyed to an analog to digital converter 69 for conversion of the analog signal to a digital signal. The separate digital signals corresponding to the fluorescent activities in lo-flow tube 43 and hi-flow tube 53 are then compared in a discriminator comparator 71. If the comparison is greater than (or less than depending upon the manner in which they are compared) a predetermined ratio, a signal is relayed to alarm transmitter 73 producing an alarm. In this manner, an alarm is generated if the amount of fluorescent activity in the hi-flow tube 53 exceeds the amount of fluorescent activity in the lo-flow tube 43 by a predetermined amount. Such a condition will occur when a test substance such as a biological agent is introduced to the reservoir 13 by means of the air intake 21 as described in more detail below.

The liquid 31 circulated in the device 11 preferably comprises water containing a buffer for pH control and microbial inhibitors. Microbial inhibitors and desirable Ph ranges for selected agents, test substances and binding and bindable substances are well-known.

The glass beads in reservoir 13 support the competitive binding substance while providing a large surface area in order to allow maximal loading and to give the widest range of sensitivity. While other materials such as filter paper, membrane filters, plastic tubes, polystyrene beads (latex), sephadex beads and agarose beads could be utilized, glass beads are preferred since they are more rigid to prevent distortion under physical stress, are inexpensive and are readily coupled to the competitive binding substance. Moreover, they are denser than other beads to provide a stable assay bed and they do not break down when exposed to various micro-organisms and changing temperatures. Preferably, the glass beads have a diameter in the range of 0.1 to 0.5 millimeters.

Operation

To prepare the device described above for operation, it must first be decided which test substance or test substances with which the device is to operate. For example, a particular microbial agent or germ for a disease such as Legionaire's disease might be chosen. Monoclonal antibodies specific to the antigen would then be prepared and attached to the glass beads 33. The analytical detection substance could then be prepared using the antigen coupled to a fluorochrome. The reservoir 13 and the device 11 is then filled with a buffered liquid suitable for the antigen, antibody, and fluorocarbon coupled antigen. The device 11 is then enclosed for operation.

In operation the motor 29 continuously circulates liquid from the reservoir 13 in parallel through the low flow conduit 15 and the high flow conduit 17 and then back to the reservoir 13. The conduits 15 and 17 are sized so that only a relatively low flow rate of liquid passes through the low flow conduit 15 and the lo-flow tube 43 and a relatively high flow rate of liquid passes through the conduit 17 and the hi-flow tube 53.

While the liquid 31 is continuously circulating, the air pump 25 is continuously introducing air into the liquid 31 in reservoir 13 through the air intake conduit 21. Air entering the liquid 31 forms bubbles which then travel to the surface 75 and then out of the reservoir through the vent/trap 27. Airborne substances are dissolved in the liquid 31 as it bubbles through the liquid in reservoir 13.

If the test substance for which the device was designed is dissolved in the liquid 31 in reservoir 13 this substance competitively binds to the competitive binding substance on the glass beads 33. Of course, the amount of test substance, analytical detection substance and competitive binding substance must be balanced in order for the competitive binding to occur. For example, if not enough analytical detection substance is present then the addition of test substance will not displace any of the analytical detection substance by competitive binding. Similarly, if too much test substance enters the system, the analytical detection substance cannot competitively bind with the excess of test substance so that no further displacement of the analytical detection substance can occur.

Assuming the proper balance, as test substance is added to the system through the air intake conduit 21 competitive binding occurs displacing analytical detection substance and changing the concentration of analytical detection substance in the liquid 31 in reservoir 13. Because of the higher flow rate through and to hi-flow tube 53 in comparison to lo-flow tube 43, the displacement produces a greater fluorescent activity in the hi-flow tube 53 in comparison to the lo-flow tube 43. This difference is detected by the detectors 51 and 59, amplified by amplifier 67, converted to a digital signal in the analog digital converters 69, compared in the discriminator comparator 71, and, if the difference is greater than a predetermined amount, an alarm signal is transmitted by alarm transmitter 73. This produces either a local or a remote alarm.

As is apparent from the above description, the method of the present invention comprises circulating a carrier fluid between a support zone fixedly containing a competitive binding substance and a detection zone. The competitive binding substance competitively binds an analytical detection substance in a test substance such that changes in concentration of test substance in the carrier fluid responsively cause changes in concentration of analytical detection substance in the carrier fluid. Changes in concentration of the analytical detection substance can be detected in the detection zone. While the circulating of the carrier fluid between the support zone and the detection zone occurs, introducing a test substance into the carrier fluid changes the concentration of the analytical detection substance in the carrier fluid. These changes in the concentration of the analytical detection substance are detected as the fluid is conveyed through the detection zone. An alarm can be activated responsive to the changes detected in said detection step.

Preferably, the method includes preparing a device of the type described above, introducing a test substance into the device and determining whether the test substance is the predetermined substance for which the device is prepared.

Since one of the most desirable uses of the present invention is as a remote automatic assay device, a desirable feature of the present invention could include incapsulating the entire device except for the reservoir, power supply and vents to protect the device from environmental factors.

By using bayonet connectors and port closures on the reservoir, removable reservoirs can be constructed with a range of desired detectable agents. This allows the device to be operated with different test substance specificity by simply changing the reservoir. It also allows analytical detection substance depletion to be corrected.

In addition to specificity for a single test substance, the method and device of the present invention can also be specific for multiple test substances. In addition, fluorochromes with differing emission wavelengths can be individually coupled to different antigens to produce distinctive analytical detection substances so that different emission wavelengths are produced with the introduction of different test substances. By utilizing filter detection systems to discriminate between wavelengths, the type of test substance could be included into the alarm transmission.

If multiple devices of the type described herein are remotely operated, the alarm transmission could encoded so as to indicate the precise location of the source of the test substance detection.

Preferably the device also includes low power indications and indications of reagent depletion. The low power indication is produced by monitoring the level of the power pack and the reagent depletion is produced by monitoring the fluorescent output in both the hi-flow tube and the lo-flow tube. Upon reaching a maximum level the device would signal reagent depletion.

Thus, the comparative assay method and device of the present invention are well adapted to attain the objects and advantages mentioned as well as those inherent therein. While presently preferred embodiments of the present invention have been described for the purpose of this disclosure, numerous changes in the construction and arrangement of parts and the steps of the methods can be made by those skilled in the art which changes are encompassed within the spirit of this invention as defined by the appended claims.

The foregoing disclosure and the showings made in the drawing are merely illustrative of the principles of this invention and are not to be interpreted in a limiting sense.

What is claimed is:

1. A device for assaying a test substance comprising:
   a carrier fluid for carrying a test substance introduced therein;
   a circulation conduit for conveying said carrier fluid and having a support zone and a detection zone therein;
   an analytical detection substance;
   a competitive binding substance fixed in said support zone and capable of competitively binding said test substance and said analytical detection substance such that changes in concentration of test substance in said carrier fluid responsively cause changes of concentration of analytical detection substance in said carrier fluid since each of said analytical detection substance and said test substance are bound to said binding substance in proportion to the concentration of test substance in said carrier fluid;
   detection means for detecting changes in concentration of said analytical detection substance in said carrier fluid as said carrier fluid is conveyed through said detection zone;
   circulation means for circulating said carrier fluid in said circulation conduit between said support zone and said detection zone; and
   introduction means for introducing said test substance into said carrier fluid.

2. The device of claim 1 wherein said carrier fluid comprises a liquid, said circulation means comprises a liquid pump, and said introduction means comprises:
   an air conduit extending into said circulation conduit; and
   an air pump for moving air through said air conduit into said carrier fluid in said circulation conduit.

3. The device of claim 1 wherein detection zone of said circulation conduit comprises a relatively low flow detection conduit allowing only a relatively low flow rate of carrier fluid therethrough and a relatively high flow detection conduit allowing a relatively high flow rate of carrier fluid therethrough, and wherein said detection means comprises:
   a low flow detector for detecting the concentration of analytical detection substance in said low flow detection conduit;
   a high flow detector for detecting the concentration of analytical detection substance in said high flow detection conduit;
   a comparator means for comparing the concentration detected by said low flow detector and the concentration detected by said high flow detector so as to indicate a changing concentration of analytical detection substance in said carrier fluid caused by the introduction of said test substance into said carrier fluid by means of said introduction means.

4. The device of claim 1 wherein said analytical detection substance comprises a fluorochrome coupled to a competitive binding agent and said detection means comprising a fluorescence detector.

5. The device of claim 4 wherein said detection zone of said circulation conduit comprises a low flow fluorescence tube allowing only a relatively low flow rate of carrier fluid therethrough and a high flow fluorescence tube allowing a relatively high flow rate of carrier fluid therethrough, and wherein said detection means comprises:
   a low flow fluorescence detector for detecting the degree of fluorescence activity in said low flow fluorescence tube;
   a high flow fluorescence detector for detecting the degree of fluorescence activity in said high flow fluorescence tube; and
   a comparator means for comparing the fluorescence activity detected by said low flow fluorescence detector and the fluorescence activity detected by said high flow fluorescence detector so as to indicate a changing concentration of fluorochrome in said carrier fluid caused by the introduction of said test substance into said carrier fluid by means of said introduction means.

6. The device of claim 5 wherein said detection means further comprises a light source for transmitting a constant amount of exciting wavelength light into said fluorescence tubes for producing fluorescent activity from said fluorochrome in said carrier fluid.

7. The device of claim 1 which further comprises an alarm connected to said detection means for signalling when changes in concentration of said analytical detection substance in said carrier fluid occur.

8. The device of claim 1 wherein said competitive binding substance comprises monoclonal antibodies.

9. The device of claim 8 wherein said monoclonal antibodies are attached to glass beads retained in said support zone of said circulation conduit.

10. A method of conducting an assay for a predetermined test substance comprising:
    preparing the device of claim 1 such that said competitive binding substance competitively binds said predetermined test substance and said analytical detection substance;
    introducing a test substance into the device of claim 1 through said introduction means; and
    determining whether said test substance is said predetermined test substance by means of said detection means.

11. A method of conducting an assay for a test substance comprising:
    continuously circulating a carrier fluid between (a) a support zone fixedy containing a competitive binding substance which competitively binds an analytical detection substance and said test substance such that changes in concentration of test substance in said carrier fluid responsively cause changes in concentration of analytical detection substance in said carrier fluid, and (b) a detection zone wherein changes in concentration of analytical detection substance in said carrier fluid can be detected;
    introducing said test substance into said carrier fluid; and
    detecting changes in concentration of said analytical detection substance in said carrier fluid as said carrier fluid is conveyed through said detection zone.

12. The method of claim 11 which further comprises activating an alarm responsive to detecting changes in concentration of analytical detection substance in said carrier fluid as said carrier fluid is conveyed through said detection zone.

13. The method of claim 11 wherein said detection zone comprises a low flow detection conduit and a high flow detection conduit, wherein said detection means comprises a low flow detector for detecting the concentration of analytical detection substance in said low flow detection conduit and a high flow detector for detecting the concentration of analytical detection substance in said high flow detector detection conduit, and wherein said circulating step comprises circulating a relatively low flow rate of carrier fluid from said support zone to said low flow detection conduit and a relatively high flow rate of carrier fluid from said support zone to said high flow detection conduit; and wherein said detecting step comprises comparing the concentration detected by said low flow detector and the concentration detected by said high flow detector so as to indicate a changing concentration of analytical detection substance in said carrier fluid caused by the introduction of a test substance into said carrier fluid.

14. The method of claim 11 wherein said analytical detection substance comprises a fluorochrome coupled to a competitive binding agent and wherein said detecting means step comprises detecting fluorescence activity.

15. The appartaus of claim 1, wherein:
said carrier fluid is further characterized as a means for carrying and continuously maintaining varying concentrations of said analytical detection substance therein.

16. The method of claim 11, wherein:
said step of continuously circulating is further characterized in that changes in concentration of test substance in said carrier fluid responsively cause permanent cumulative changes in concentration of analytical detection substance in said carrier fluid.

* * * * *